United States Patent [19]

Larsson et al.

[11] 4,138,216

[45] Feb. 6, 1979

[54] DEVICE FOR MONITORING ETHYLENE OXIDE STERILIZATION PROCESS

[75] Inventors: Raymond P. Larsson, Denville; Robert J. Witonsky, Princeton, both of N.J.

[73] Assignee: Bio-Medical Sciences, Inc., Fairfield, N.J.

[21] Appl. No.: 864,043

[22] Filed: Dec. 23, 1977

[51] Int. Cl.² ............................................ G01N 31/22
[52] U.S. Cl. ..................................... 422/56; 252/408; 422/58
[58] Field of Search .......... 23/253 TD; 116/114 AM; 252/408

[56] References Cited

U.S. PATENT DOCUMENTS

| 3,932,134 | 1/1976 | Fang et al. | 23/253 TP |
| 3,946,611 | 3/1976 | Larsson | 73/356 |
| 3,981,683 | 9/1976 | Larsson et al. | 23/253 TP |
| 3,996,007 | 12/1976 | Fang et al. | 23/253 TP |
| 4,042,336 | 8/1977 | Larsson | 23/253 TP |

OTHER PUBLICATIONS

Brewer et al., J. Pharmaceutical Sciences, Jan. 1966, pp. 57-59.

Royce et al., J. Pharm. & Pharm. II, Suppl. 294t-298t.

Primary Examiner—Robert M. Reese
Attorney, Agent, or Firm—Anthony Lagani, Jr.

[57] ABSTRACT

A device for monitoring ethylene oxide sterilization processes comprising a wick means impregnated with an ethylene oxide responsive chemical compound, a pH sensitive dye and a quantifier mounted on a backing strip and sealed with a cover strip to form an envelope having one edge at which the wick means is exposed. The device is responsive to time, temperature and relative humidity as well as ethylene oxide concentration.

10 Claims, 4 Drawing Figures

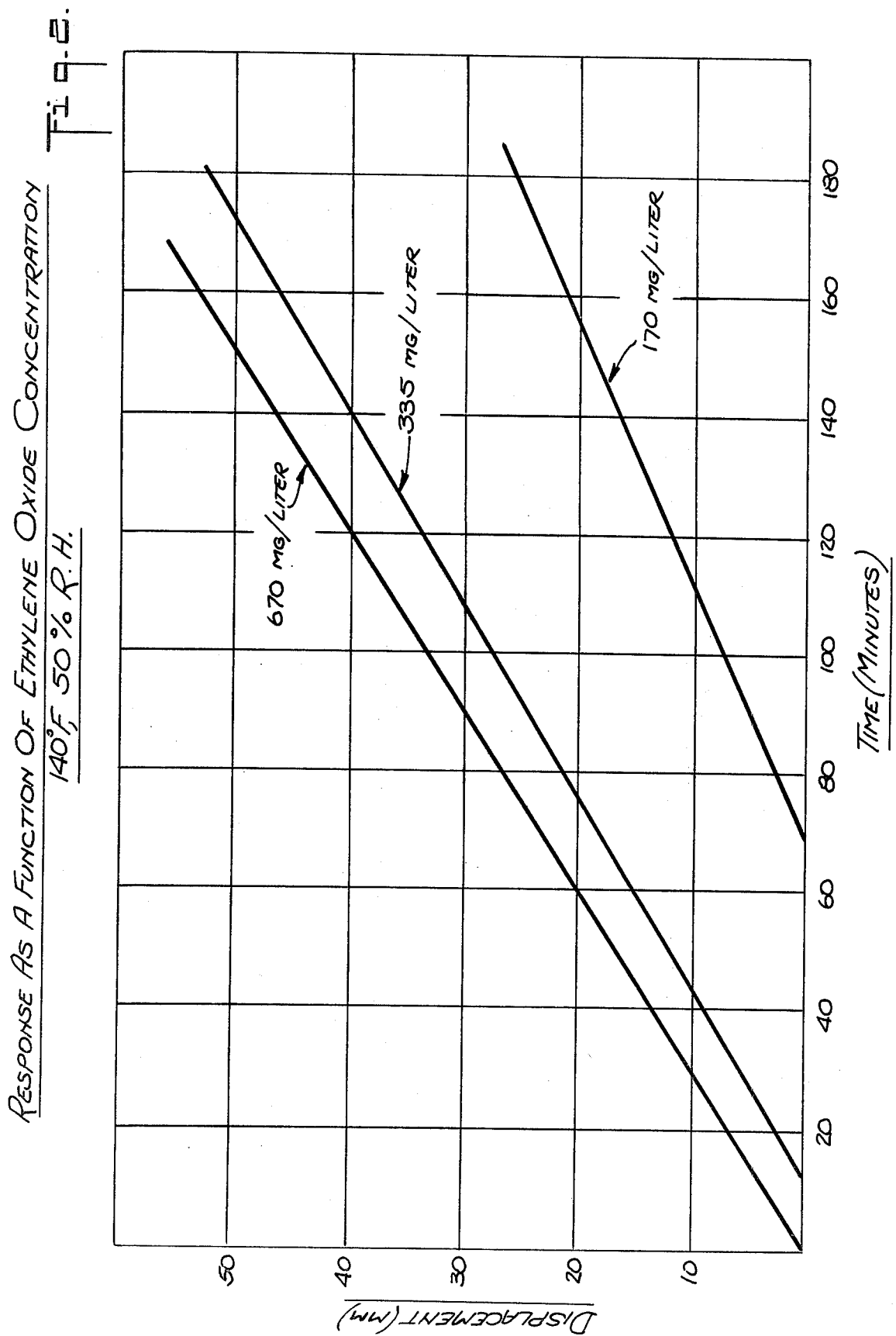

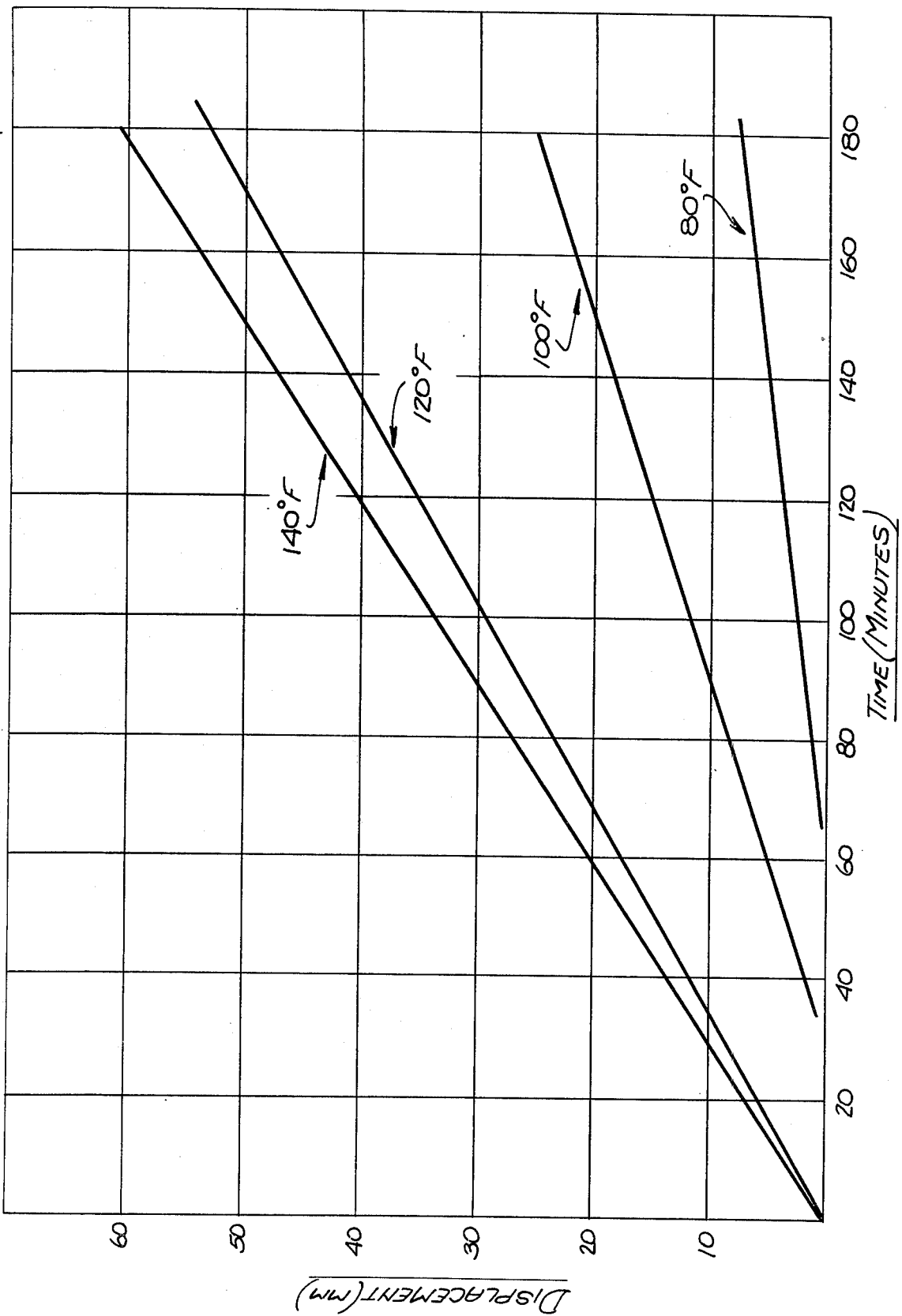

DEVICE FOR MONITORING ETHYLENE OXIDE STERILIZATION PROCESS

BACKGROUND OF THE INVENTION

The sterilization of surgical supplies and parenteral drugs is a carefully controlled process. An effective commonly used method of sterilization is by the use of steam under pressure. However, many surgical instruments and supplies are adversely affected by heat, and sterilization at high temperature is not practical for those items.

An outgrowth of agricultural and industrial fumigation is gaseous sterilization using ethylene oxide as the sterilant. The advantages of gaseous sterilization are: sterilization is at low temperatures thus avoiding damage to heat and moisture-sensitive materials, objects or items can be terminally sterilized in their packages and the equipment required is simple.

The parameters which affect sterilization processes using ethylene oxide are exposure time, gas concentration, temperature and humidity. When diluted ethylene oxide is added relative humidities below about 30% RH limit the effectiveness of the process. High humidities, e.g., above 90%, also result in inadequate processing. The time required for sterilization is inversely proportional to gas concentration and decreases with increasing temperature. Hence, a useful process control must be sensitive to humidity, temperature, gas concentration and the processing time elapsed.

The gas concentration generally used is about 450 mg/lt to about 1,500 mg/lt while processing temperature may vary from about 70° F to about 140° F.

In order to achieve sterilization processing times may vary from about 45 minutes to several hours. Of course, humidity must be in the proper range to effectively sterilize, e.g., 40-80% R.H.

The classical method for determining the effectiveness of any microbial sterilization process is to include in the system exposed to the sterilizing process a suitable resistant organism. For ethylene oxide sterilization the organisms used are the spores of *Bacillus subtilis var. niger*. These spores exhibit high resistance to ethylene oxide. Such a method suffers from the fact that at least several days are required to culture the spores in order to verify the effectiveness of the sterilization process. Additionally, the spores, being living organisms, the rate at which they are killed is a logarithmic relationship with time, resulting in a broad time window between initial and complete spore kill.

In the field of heat sterilization various physical indicators have been developed to monitor the sterilization process. These vary in quality from the simplest, melt indicators which merely show that a particular temperature has been achieved to a sophisticated device which responds to time, temperature and steam known as Thermolog ® S, see for example U.S. Pat. No. 3,946,611.

Various physical monitors have been developed in an attempt to monitor ethylene oxide sterilization. 4(4-Nitrobenzyl)pyridine has been used as an indicator when applied to a paper strip; see for example *Journal of Pharmaceutical Sciences*, Brewer et al., pages 57-59, January 1966. Other compounds including pyridines and quinolines have also been used; see U.S. Pat. No. 3,627,469. An ink composition has been prepared as a telltale for ethylene oxide sterilization which utilizes the fact that $MgCl_2$ reacts with ethylene oxide to produce $Mg(OH)_2$ which is detected by a pH sensitive dye; see U.S. Pat. No. 3,098,751. This same mechanism has been used to prepare a physical sterilization indicator by depositing the reactants on an absorbent material and enclosing the composition in a sealed envelope of gas permeable film such as polyethylene; see Royce and Bower "An Indicator Control Device for Ethylene Oxide Sterilization." *J. Pharm. and Pharm.* 11, Suppl. 294T-298T.

Recently, a device has been developed which integrates the time-temperature history of a process by presenting a color change which moves along a wick in response to the presence of an acidic or basic gaseous atmosphere; see U.S. Pat. Nos. 3,946,611 and 3,932,134.

SUMMARY OF THE INVENTION

It has surprisingly been found that a physical monitor for the indication of ethylene oxide sterilization can be made utilizing a wick impregnated with an ethylene oxide responsive compound, e.g., $MgCl_2$ and sealing all but one end of the wick in an ethylene oxide impervious film. The wick may be made of any suitable absorbent material such as paper, cloth, etc. into which the indicator system can be deposited from solution. In addition to the ethylene oxide responsive compound the wick contains a pH sensitive dye and a quantifier which serves to control the time response of the device. Surprisingly the device is responsive to humidity levels as well as gas concentration and temperature.

BRIEF DESCRIPTION OF DRAWINGS

FIG. 2 — Plot of Device Response As a Function of Ethylene Oxide Concentration.

FIG. 3 — Plot of Device Response As a Function of Temperature.

DETAILED DESCRIPTION

Figure 1A:
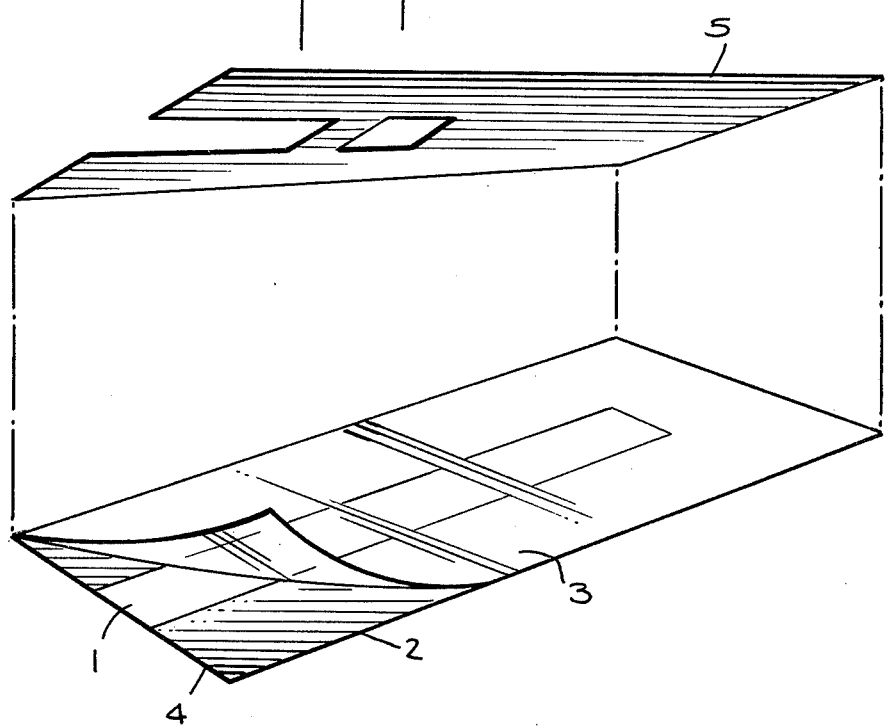
FIG. 1a — Exploded View of Device Showing Structure.

This invention relates to a physical process monitor to measure the effectiveness of ethylene oxide sterilization. More particularly it relates to a wick type monitor which is responsive to ethylene oxide concentration, temperature, time and humidity.

The monitor comprises a wick impregnated with a chemical compound which will react with ethylene oxide to form a basic product and a pH sensitive dye which will present a visual indication of the presence of the basic reaction product. Additionally, the wick has incorporated in it a quantifier compound which determines the rate at which the response to the presence of ethylene oxide appears along the length of the wick. The color change proceeds along the wick in an analog fashion at a rate which for a given composition is a function of gas concentration, temperature and humidity.

The wick is enclosed in an envelope having one open end from which the wick protrudes. The envelope is constructed of an ethylene oxide impermeable film.

Illustrative examples of chemical compounds suitable for use in the instant invention include $MgCl_2$, $FeCl_2$, $ZnCl_2$, and the hydrates of these salts. A particularly preferred compound is the hydrate of magnesium chloride ($MgCl_2 \cdot 6H_2O$).

As used in the specification and claims the term "ethylene oxide responsive chemical compound" means chemical compounds which react with ethylene oxide to produce a basic reaction product of which the foregoing compounds are illustrative examples.

The material used for the wick is not critical. It need only be sufficiently absorbent to take up the solution containing the chemical compound. Any fabric such as polyamide polyester, cotton etc. whether woven or non-woven is suitable. Of course, the material selected must not be deleteriously effected by the basic reaction product or ethylene oxide. Paper is the preferred wick material.

Illustrative examples of the pH sensitive dyes which can be used in the practice of this invention are bromphenol blue, thymol blue, and xylenol blue. The pH sensitive dye preferably has at least one $pK_a$ value which is less than 8; more preferably less than 7. The preferred pH sensitive dye is bromphenol blue.

The term pH sensitive dye is used in the specification and claims means a pH sensitive dye with at least one $pK_a$ value which is less than 8.

The quantifier material is a compound which reacts preferentially with the basic reaction product thereby neutralizing it and preventing a color change of the pH sensitive dye. The preferred quantifiers are acids and acid salts of low volatility. Illustrative examples of the quantifiers of this invention are tartaric acid, oxalic acid, citric acid, sodium bisulfate, etc.

The term quantifier as used in the specification and claims means an acidic compound which has a $pK_a$ value less than 6 which reacts with the base produced by the reaction of ethylene oxide with the ethylene oxide responsive chemical compound and is thereby neutralized.

Any material which is impervious to ethylene oxide may be used as the envelope to contain the wick means. Of course, at least a part of the material must be transparent in order to display the wick. The preferred envelope materials are ethylene oxide impervious polymeric films. However metal foils may be used as a part of the envelope, e.g. aluminum foil or aluminum foil coated with polyethylene.

Illustrative examples of ethylene oxide impervious films are trifluoropolyethylene, polycarbonates, polyvinylidene chloride or polyesters, in particular the ester of ethylene glycol and terephthalic acid (Mylar).

In preparing the wick means the wick composition is impregnated with a solution of ethylene oxide responsive chemical compound, pH sensitive dye and quantifier in a suitable solvent. Preferably the solvent is a volatile material such as $C_1$-$C_3$ alcohols. More preferably the solvent is a mixture of water and alcohol. In its preferred embodiment the water/alcohol mixture comprises about 40 to about 70% alcohol; more preferably about 50% methanol.

The term "solvent" as used in the specification and claims means a normally liquid compound which is a solvent for the ethylene oxide responsive chemical compound, the pH sensitive dye and the quantifier which can be readily removed from the wick by evaporation and is inert with respect to such component during the period of impregnation and dyeing.

Illustrative examples of solvents suitable for use in preparation of the wick means in the practice of this invention are ethanol, methanol, methyl acetate, ethyl acetate, propanol, butanol, water and mixtures thereof. The preferred solvents are methanol, ethanol, water and mixtures of water with these solvents.

Referring now to FIG. 1a, the wick, 1, is mounted on an adhesive coated backing 2. A transparent ethylene oxide impervious cover strip, 3, is adhered to the backing strip, 1, and completely enclosing the wick except for the open end, 4. When the cover strip, 3, is adhered to the backing strip the wick, 1, is exposed only along the open end, 4. Of course the wick may protrude beyond the edge, 4, but such a construction offers no particular advantage.

Figure 1B:
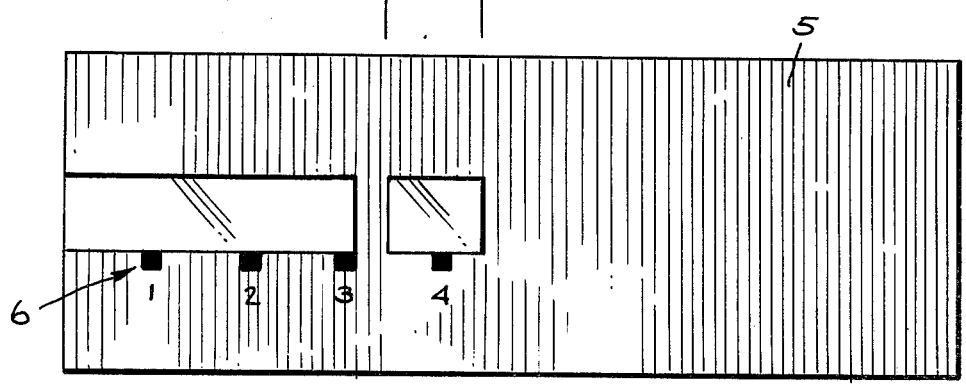
FIG. 1b — Plan View of Device Showing Label and Scale.

In another embodiment the cover strip is adhered to the backstrip by heat sealing. The backstrip of course must also be ethylene oxide impervious. It need not be transparent but can be the same material as the cover strip. As shown in FIG. 1b, for convenience of use a label, 5, may be adhered to the cover strip so that a scale, 6, may be imprinted thereon. It is of course obvious that the backing strip and cover strip can be a continuous sheet folded upon itself to form an envelope.

The advantages of the instant invention may be more readily appreciated by reference to the following examples.

EXAMPLE I

An ethylene oxide indicator was prepared as shown in the figure except that the exposed end of the wick was enclosed by polypropylene to act as a rate controlling film to control the rate at which ethylene oxide enters the envelope and is absorbed by the wick means.

The wick means in this example comprised a 6 mil thick piece of Whatman #1 filter paper 80 mm long and 6.5 mm wide. The wick was impregnated with a solvent solution composition comprising:

| Component | Wt. % |
|---|---|
| $MgCl_2.6H_2O$ | 0.13 |
| $Na_2HSO_4$ | 0.10 |
| Bromphenol Blue | 0.005 |
| Methanol | 99+ |

The wick was impregnated with the solvent solution, excess fluid pressed from it and allowed to dry. The backing strip and cover strip used were mylar film (ethylene glycol-terephthalic acid polyester) about 1 mils thick. The strips were adhered together by an acrylic adhesive.

The test chamber comprised a 500 cc glass chamber with O-ring joint and teflon valve capable of connection to a vacuum system and an ethylene oxide source. Additionally, the test chamber was in communication with a humidity chamber which maintained a constant humidity in the test chamber by means of a concentrated solution of sodium bisulfate (ca 52% RH) as a humidistat. The solution was contained in a microporous polyethylene bag.

The indicators were placed in the test chamber and the system evacuated. After allowing the chamber to equilibrate with the humidistat the test chamber was charged with a mixture of freon 12 and ethylene oxide (88/12) to a total pressure of 800 torr and maintained at 140° F using a water bath. Readings on the indicator were taken at five minute intervals by measuring the length (mm) of migration of color change along the wick.

It was noted that after removal of the indicator from the test chamber the color change continued to migrate down the length of the wick. It was theorized that this was caused by ethylene oxide trapped within the device after evacuation of the system before terminating the test. It was also shown that the indicator paper could not come into equilibrium with the humidistat during the test period.

EXAMPLE II

The experiment of Example I was repeated except that the rate controlling film was deleted and the wick was left exposed directly to the ethylene oxide atmosphere.

At completion of the test there was no further migration of the color bar along the wick. Also humidity equilibration was established. Hence, it is evident that the wick of the indicator device of this invention cannot be completely enclosed. Otherwise erroneous results will be obtained resulting from trapped ethylene oxide within the device, and a humidity response which is not representative, that of the ethylene oxide containing atmosphere.

EXAMPLE III

The experiment of Example II was repeated using a device comprisig a strip of Whatman #1 filter paper (80 mm × 6 mm) which had been impregnated in the manner of Example I with a methanol impregnation solution comprising 0.3 moles $MgCl_2.6H_2O$, 0.25 molar tartaric acid and 0.002 molar bromphenol blue as the wick and one mil Mylar film as the cover strip adhered to an aluminum foil backing by acrylic adhesive. The wick was exposed at one end of the envelope so formed as in FIG. 1b. The purpose of the test was to determine the effect of ethylene oxide concentration on the reading obtained on the device as measured by migration of the color bar along the device.

FIG. 2 shows the color bar displacement in (mm) as a function of time for various ethylene oxide concentrations. All runs were carried out at 50% RH and 140° F.

It will be noted from the displacement of each of the curves that the device of this invention is sensitive to ethylene oxide concentration. This sensitivity is more marked at lower concentrations of ethylene oxide, below 300 mg/liter, and less pronounced at high concentrations in keeping with similar effects of gas concentrations on destroying b. subtilis spores.

EXAMPLE IV

The experiment of Example III was repeated using constant ethylene oxide concentration (670 mg/liter) and constant relative humidity (50% RH) in order to test the temperature sensitivity of the device.

FIG. 3 shows a plot of color bar dislacement (mm) as a function of time for four temperatures ranging from 80° F to 140° F. It is evident from the slopes and displacement of the curves that the device of this invention is temperature sensitive. The temperature coefficient, $Q_{10}$, for destroying spores with ethylene oxide is reported to be in the range of 1.4 to 2.0. The $Q_{10}$ for this device is within this range.

EXAMPLE V

The experiment of Example IV was repeated at 120° F and 140° F for an ethylene oxide concentration of 670 mg per liter. The relative humidity was varied between 0 and 100% RH in order to determine the humidity sensitivity of the device. Readings were taken after 1 hr. and 2 hrs. of exposure to ethylene oxide. The results are tabulated below in Table I.

TABLE I

| | Humidity Sensitivity of Indicator | | | |
|---|---|---|---|---|
| T ° F | Conc. mg/liter | RH % | 1 hr. mm | 2 hr. mm |
| 120 | 670 | 100 | 6 | 12 |
| 120 | 670 | 50 | 17 | 35 |
| 120 | 670 | 0 | erasure | erasure |
| 140 | 670 | 100 | 11 | 30 |
| 140 | 670 | 74 | 23 | 39 |
| 140 | 670 | 50 | 20 | 40 |
| 140 | 670 | 30 | erasure | erasure |
| 140 | 670 | 0 | erasure | erasure |

At humidities of 30% RH and below the color change produced by the ethylene oxide reaction is reversible and the blue color will fade within a few hours after removal from the ethylene acidic atmosphere. This result is wholly unexpected but results in a device which will not give a stable reading at low humidities. At humidities above 85% RH the rate at which the color bar migrates down the device slows appreciably. These two humidity effects coincide with the areas in which there is difficulty in sterilization using ethylene oxide as a fumigant. At low humidities little or no destruction of spores results. At the high humidity the chemical death rate for the spore is slower than in the 40-80% RH range.

EXAMPLE VI

The experiments of Example IV were repeated under various conditions in order to correlate color bar migration with spore death in an ethylene oxide sterilization process. The spore used was *Baccilus subtilis*.

Filter papers were cut into 40 mm × 3 mm strips, sterilized with steam, dried, and impregnated with 1-2 × $10^5$ spores of *Baccilus subtilis*. These strips were aseptically transferred to glassine envelopes and sealed. Several of these spores strips were placed side by side with indicators of this invention in surgical packs and processed with 12% ethylene oxide in a hospital sterilizer under different sets of conditions. After the completion of the cycle of the indicators were removed from the packs, their color bar migrations measured and recorded. The spores were aseptically tranferred to a growth medium and incubated. Viability was determined after this period.

The results are shown in Table II.

TABLE II

| Expt. No. | Ethylene Oxide Concentration (Mg/L) | Temperature (° F.) | Relative Humidity (%) | Time (min.) | Color Bar Reading (mmp*) | 1-2 × $10^5$ B.subtilis |
|---|---|---|---|---|---|---|
| 1 | 300 | 120 | 50-60 | 7 | 0,0,0,0 | 10/10 |
| 2 | 300 | 120 | 50-60 | 14 | 2,2,2,2 | 10/10 |
| 3 | 300 | 120 | 50-60 | 30 | 4,3,5,5 | 10/10 |
| 4 | 300 | 125 | 50-60 | 27 | 12,12,10,12 | 0/10 |
| 5 | 300 | 130 | 50-60 | 122 | 23,23,23,23 | 1/10 |
| 6 | 300 | 130 | 50-20 | 90 | 18,18,18,18 | 0/10 |
| 7 | 300 | 130 | 50-60 | 50 | 12,12,12,12 | 0/10 |
| 8 | 600 | 122 | 88 | 5 | 0,0,0,0 | 9/10 |
| 9 | 600 | 124 | 58 | 17 | 9,9,9,10 | 6/10 |

TABLE II-continued

| Expt. No. | Ethylene Oxide Concentration (Mg/L) | Temperature (° F.) | Relative Humidity (%) | Time (min.) | Color Bar Reading (mmp*) | $1\text{-}2 \times 10^5$ B.subtilis |
|---|---|---|---|---|---|---|
| 10 | 600 | 124 | 75 | 30 | 10,13,10,13 | 9/10 |

With the exception of expt. #5 were one spore strip cultured positive and nine negative, the safe mark appears at about a 15 to 18 mm color bar reading. Example No. 5 demonstrates the statistical nature of spore destruction since only 90% of the spores were destroyed after 2 hours at 300 mg/liter and 130° F. This should be compared with experiment No. 7 where ten of ten spore strips cultured negative for conditions identical to those of Expt. No. 5 except that the exposure time was only half as long, i.e., 1 hour.

EXAMPLE VII

The device of this invention as described in Example III was tested in several different models of Hospital sterilizers. The results are shown in Tables III, IV and V.

TABLE III
3M Model 200 Sterilizer
THERMALOG*G GAS INTEGRATOR

| Gas Con. | Temp. | Humidity | Hold Time | Color Bar Read (mm) | Spore Test (+/−) |
|---|---|---|---|---|---|
| 67 gram cartridge | 85° | wet sponge aspiration | 3 hrs. | 40 | − |
| | 85° | | 3 hrs. | 40 | − |
| | 85° | | 3 hrs. | 40 | |
| | 85° | | 3 hrs. | 40 | |
| | 85° | | 3 hrs. | 40 | |
| | 85° | | 3 hrs. | 40 | |
| | 85° | | 3 hrs. | 40 | |
| | 85° | | 3 hrs. | 40 | |

TABLE IV
AMSCO 979 G S Sterilizer*

| Runs | Temp. | Humidity | Hold Time | Color Bar Read (mm) | Spore Test (+/−) |
|---|---|---|---|---|---|
| 1 | 130° | 50% | 4½ hrs. | 35 | − |
| 2 | 130° | 50% | 4 hrs. | 40 | − |
| 3 | 130° | 50% | 4 hrs. | 40 | − |
| 4 | 130° | 50% | 4½ hrs. | 40 | − |
| 5 | 130° | 50% | 4½ | 35 | − |
| 6 | 130° | 50% | 4½ hrs. | 40 | − |
| 7 | 130° | 50% | 4½ hrs. | 30 | − |
| 8 | 130° | 50% | 4½ hrs. | 40 | − |

*Gas concentration - 88% freon, 12% ethylene oxide at 600 mg/liter of ethylene oxide TABLE V
3M Model 400 Sterilizer

| Gas Con. | Temp. | Humidity | Hold Time | Color Bar Read (mm) | Spore Test (+/−) |
|---|---|---|---|---|---|
| 134 gram cartridge | 85° | water injection | 4 hrs. | 40 | − |
| | 85° | | 4 hrs. | 40 | − |
| | 85° | | 4 hrs. | 40 | − |
| | 85° | | 4 hrs. | 40 | − |
| | 85° | | 4 hrs. | 40 | − |
| | 85° | | 4 hrs. | 40 | − |
| | 85° | | 4 hrs. | 40 | − |
| | 85° | | 4 hrs. | 40 | − |

These results illustrate the reliability of the device of this invention in actual hospital ethylene oxide cycles. In every example, both for pure ethylene oxide cycles and for dilute ethylene oxide cycles the indicator showed adequate processing and all challenge spores were dead.

EXAMPLE VIII

The humidity studies of EXAMPLE V were repeated at an ethylene oxide concentration of 700 mg/liter and 140° F. Readings were taken at various time intervals. The results are shown in Table VI.

TABLE VI

| Relative Humidity | Color Bar Reading (mm) | | | |
|---|---|---|---|---|
| | 30 min. | 60 min. | 90 min. | 120 min. |
| 0 | * | * | * | * |
| 20 | * | * | * | * |
| 50 | 10 | 20 | 31 | 39 |
| 74 | 12 | 23 | 33 | 39 |
| 95 | 1 | 10 | 20 | 28 |

*reversible erasures of color change

These results confirm the humidity sensitivity of the device of this invention. In particular it has been demonstrated that the device can distinguish between high and low humidity exposure and that in the 40-75% RH range the device gives consistent comparative results.

EXAMPLE IX

Since at low temperatures sterilization times are quite long it was of interest to compare the color bar readings as a function of temperature over the usual four hour hospital sterilization cycle. Table VII shows the results obtained at various temperatures using 700 mg/liter of ethylene oxide (ethylene oxide/freon-12/88) and 50% RH.

TABLE VII

| | Temperature Sensitivity Response, mm | | | |
|---|---|---|---|---|
| T° F | 1 hr. | 2 hrs. | 3 hrs. | 4 hrs. |
| 80 | 0 | 0 | 5 | 10 |
| 100 | 2 | 14 | 25 | 38 |
| 120 | 16 | 35 | 52 | — |
| 140 | 20 | 40 | 58 | — |

EXAMPLE X

A product manufactured by Anderson Corporation (ANPRO) and sold under the trademark "AN 87 Dosimeter" as an ethylene oxide sterilization indicator was evaluated in a study similar to that of EXAMPLE IV and compared to the device of this invention. The ANPRO device consists of a capillary tube sealed at one end only and filled with a resin which contains a color sensitive ethylene oxide indicator. The device responds much like the device of this invention in that a color bar migrates along the tube. The AN 87 device migrated at the same rate in relative humidities of 0, 50 and 100% with no subsequent erasure.

It is evident from the foregoing examples that the device of this invention is a suitable tool for the monitoring of ethylene oxide sterilization processes. The advantages of this device over prior devices are many. The reading obtained is a clearly usable reading not dependent on detecting variations in color changes. The device is sensitive to temperature and ethylene oxide concentration as well as humidity. Furthermore, it is capable of distinguishing between low and high humidity conditions and therefore can be used to diagnose problems in the sterilization process.

What is claimed is:

1. A device for monitoring an ethylene oxide sterilization process which comprises:
   (a) a wick means said wick means being impregnated with an ethylene oxide responsive chemical compound, a pH sensitive dye and a quantifier;
   (b) a backing strip upon which the wick means is mounted; and
   (c) a cover strip comprising an ethylene oxide impervious film adhered to said backing strip thereby forming an envelope enclosing said wick means, the wick means having one end exposed along one edge of said envelope.

2. The device of claim 1 wherein the quantifier is tartaric acid, oxalic acid, citric acid or sodium bisulfate.

3. The device of claim 1 wherein the cover strip is adhered to the backing strip using an acrylic adhesive.

4. The device of claim 1 wherein the cover strip is adhered to the backing strip by heat sealing.

5. The device of claim 1 wherein the envelope comprises a continuous piece of ethylene oxide impervious film folded upon itself to form said envelope.

6. The device of claim 1 wherein
   (a) the ethylene oxide responsive chemical compound is $MgCl_2 \cdot 6H_2O$;
   (b) the ethylene oxide impervious cover strip is a ethylene glycol-terephthalic acid polyester;
   (c) the pH sensitive dye is bromphenol blue;
   (d) the quantifier is tartaric acid; and
   (e) the wick means comprises a paper strip.

7. The device of claim 1 wherein the chemical compound is $MgCl_2$, $FeCl_2$, $ZnCl_2$ or the hydrates thereof.

8. The device of claim 7 wherein the compound is $MgCl_2 \cdot 6H_2O$.

9. The device of claim 1 wherein the pH sensitive dye has at least one pKa value of less than 7.

10. The device of claim 9 wherein the dye is bromphenol blue, thymol blue or xylenol blue.

* * * * *

REEXAMINATION CERTIFICATE (3224th)
United States Patent [19]
Larsson et al.

[11] B1 4,138,216
[45] Certificate Issued Jun. 17, 1997

[54] DEVICE FOR MONITORING ETHYLENE OXIDE STERILIZATION PROCESS

[75] Inventors: Raymond P. Larsson, Denville; Robert J. Witonsky, Princeton, both of N.J.

[73] Assignee: Info Chem. Inc., Somerville, N.J.

Reexamination Request:
No. 90/003,898, Jul. 21, 1995

Reexamination Certificate for:
Patent No.: 4,138,216
Issued: Feb. 6, 1979
Appl. No.: 864,043
Filed: Dec. 23, 1977

[51] Int. Cl.⁶ .................................................. G01N 31/22
[52] U.S. Cl. ................................. 422/58; 422/56; 422/61; 436/1; 436/128; 252/408
[58] Field of Search .................................. 422/56–58, 61, 422/28, 34; 436/142, 163, 164, 1, 128; 252/408

[56] References Cited

U.S. PATENT DOCUMENTS

| | | | |
|---|---|---|---|
| 2,998,306 | 8/1961 | Huyck et al. | 23/254 |
| 3,324,723 | 6/1967 | Ritchie et al. | 73/358 |
| 3,479,877 | 11/1969 | Allen et al. | 73/358 |
| 3,932,134 | 1/1976 | Fang et al. | 23/253 TP |
| 4,042,336 | 8/1977 | Larsson | 23/253 TP |
| 4,145,186 | 3/1979 | Andersen | 23/232 R |

*Primary Examiner*—Lyle Alfandary-Alexander

[57] ABSTRACT

A device for monitoring ethylene oxide sterilization processes comprising a wick means impregnated with an ethylene oxide responsive chemical compound, a pH sensitive dye and a quantifier mounted on a backing strip and sealed with a cover strip to form an envelope having one edge at which the wick means is exposed. The device is responsive to time, temperature and relative humidity as well as ethylene oxide concentration.

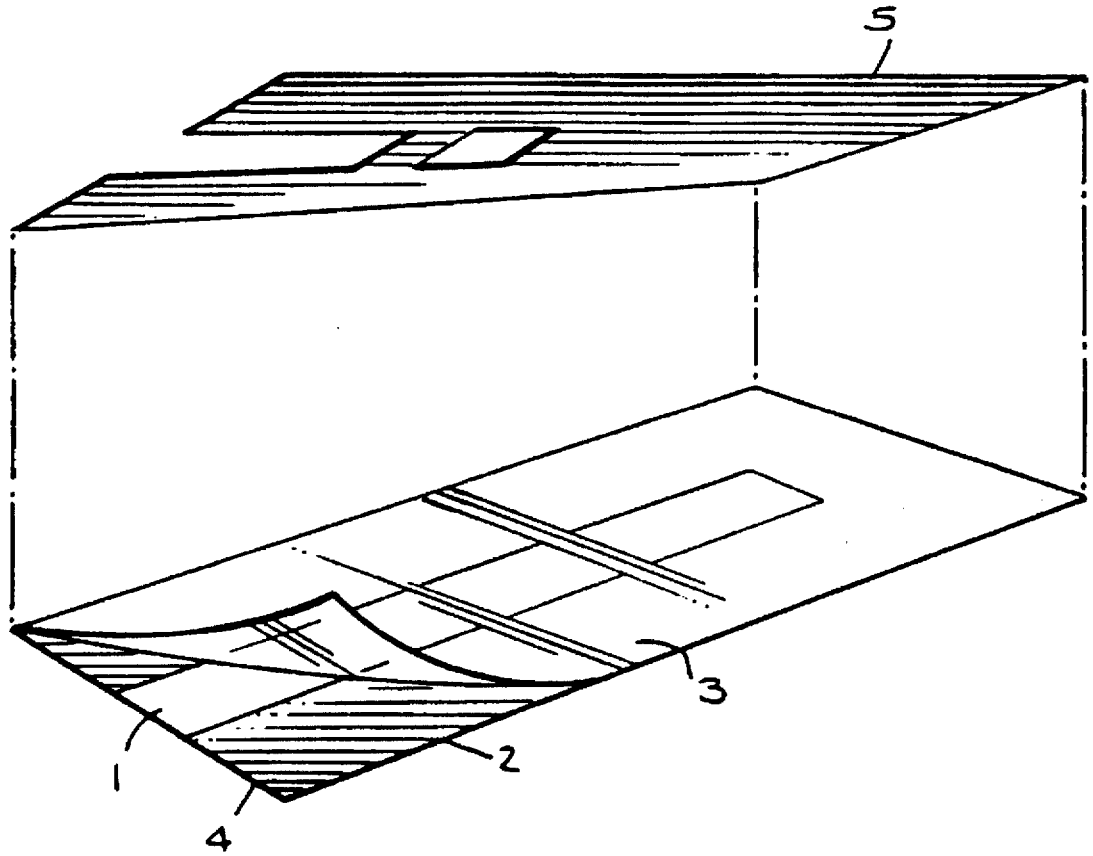

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 3 and 4 are cancelled.

Claim 1 is determined to be patentable as amended.

Claims 2 and 5–10, dependent on an amended claim, are determined to be patentable.

New claim 11 is added and determined to be patentable.

1. A device for monitoring an ethylene oxide sterilization process [which comprises] *consisting essentially of*:
   (a) a wick means, said wick means being impregnated with an ethylene oxide responsive chemical compound, a pH sensitive dye and a quantifier;
   (b) [a] *an ethylene oxide impervious* backing strip upon which the wick means is mounted *said backing strip being coated with an adhesive*; and
   (c) [a] *an adhesive free* cover strip comprising an ethylene oxide impervious film adhered to said backing strip *by means of the backing strip adhesive coating* thereby forming an envelope enclosing said wick means, the wick means having one end exposed along one edge of said envelope, *and a surface of the wick juxtaposed to the cover strip not adhered to the film*.

*11. A device for monitoring an ethylene oxide sterilization process which comprises:*
   *(a) a wick means, said wick means being impregnated with an ethylene oxide responsive chemical compound, a pH sensitive dye and a quantifier;*
   *(b) an ethylene oxide impervious backing strip upon which the wick means is mounted; and*
   *(c) a cover strip comprising an ethylene oxide impervious film, said cover strip being heat sealed to said backing strip thereby forming an envelope enclosing said wick means, the wick means having one end exposed along one edge of said envelope, and at least one surface of said wick means juxtaposed to the envelope film not adhered to the film.*

* * * * *